US011621076B2

(12) United States Patent
Dong et al.

(10) Patent No.: US 11,621,076 B2
(45) Date of Patent: Apr. 4, 2023

(54) MACHINE LEARNING SYSTEM AND METHOD FOR PET HEALTH RECORDS

(71) Applicant: Pawprint, Inc., San Francisco, CA (US)

(72) Inventors: Emily Dong, San Francisco, CA (US); Sinan Ozdemir, Arlington, VA (US); Eric Choi, Bellevue, WA (US); Jonathan Levine, Dix Hills, NY (US)

(73) Assignee: Snout, Inc., Los Angeles, CA (US)

( * ) Notice: Subject to any disclaimer, the term of this patent is extended or adjusted under 35 U.S.C. 154(b) by 902 days.

(21) Appl. No.: 16/421,368

(22) Filed: May 23, 2019

(65) Prior Publication Data

US 2019/0362847 A1 Nov. 28, 2019

Related U.S. Application Data

(60) Provisional application No. 62/676,245, filed on May 24, 2018.

(51) Int. Cl.
| | |
|---|---|
| *G06E 1/00* | (2006.01) |
| *G16H 50/20* | (2018.01) |
| *G06N 3/08* | (2023.01) |
| *G06K 9/62* | (2022.01) |
| *A61B 5/00* | (2006.01) |
| *G06N 20/20* | (2019.01) |
| *G06F 40/284* | (2020.01) |

(52) U.S. Cl.
CPC .......... *G16H 50/20* (2018.01); *A61B 5/7282* (2013.01); *G06K 9/6227* (2013.01); *G06N 3/08* (2013.01); *G06N 20/20* (2019.01); *G06F 40/284* (2020.01)

(58) Field of Classification Search
CPC .... G16H 50/20; A61B 5/7282; G06K 9/6227; G06N 3/08; G06N 20/20; G06N 3/0445; G06N 7/005; G06N 20/10; G06F 40/284
USPC ......................................................... 706/20
See application file for complete search history.

(56) References Cited

U.S. PATENT DOCUMENTS

| | | | |
|---|---|---|---|
| 11,317,059 B1 * | 4/2022 | Lanatta | H04L 65/1089 |
| 2008/0172737 A1 * | 7/2008 | Shen | G16H 10/60 726/21 |
| 2018/0144099 A1 * | 5/2018 | Leon | H04L 67/02 |
| 2018/0293241 A1 * | 10/2018 | Chittar | G06N 20/20 |

* cited by examiner

*Primary Examiner* — Tai T Nguyen
(74) *Attorney, Agent, or Firm* — Cognition IP, P.C.; Edward Steakley

(57) ABSTRACT

A pet medical text recognizer may include one or more machine learning classifiers. The one or more machine learning classifiers may be trained using training data to associate raw text with pet clinical event codes. A performance metric may be provided, and the highest performing classifier according to the performance metric may be selected as the model for the pet medical text recognizer. The pet medical text recognizer may accept input text from a veterinary practice management system and generate a pet clinical event code for the text. A set of codes associated with a single pet may be aggregated into a pet health record.

20 Claims, 4 Drawing Sheets

Veterinary Practice Management System
100

- Patients
  101
- Clients
  102
- Invoices
  103
- Schedule / Appointments
  104
- Reminders
  105
- Medical Notes
  106
- Pet Health Records
  107

FIG. 1

MACHINE LEARNING SYSTEM AND METHOD FOR PET HEALTH RECORDS

CROSS-REFERENCE TO RELATED APPLICATIONS

This application claims the benefit of U.S. Provisional Patent Application No. 62/676,245, filed May 24, 2018, which is hereby incorporated by reference in its entirety.

FIELD OF THE INVENTION

The present invention relates to methods and systems for using artificial intelligence to generate health records for pets.

BACKGROUND

In the veterinary health field, there are no standardized codes to record what vaccinations, medications, or procedures were applied to client's pets. Instead information is stored as free form text, which is difficult for both humans and computers to analyze. One problem that arises is that two sets of veterinary notes written in text may refer to the same clinical event, such as a treatment or diagnosis, but would not be recognized as such because there is no standardized code to identify it as such. It can be difficult for a veterinary practitioner to review the medical history of a pet to ensure that all of the necessary treatments were provided because of the lack of standardized codes.

It would be desirable and novel in the art to provide a standardized code system for pets. One challenge of creating a standardized code system is the difficulty in training veterinary practitioners to correctly enter the right codes. Moreover, it would be time consuming and tedious to code the many pet visits that occurred prior to the adoption of the standardized code system. Veterinary practitioners may also enter different text referring to the same event, making human coding more difficult.

It would be desirable to provide a software and hardware system using machine learning to automatically code pet veterinary visits according to a standardized pet medical coding system.

SUMMARY OF THE INVENTION

Embodiments relate to methods of generating a pet health record that includes standardized codes of clinical events associated with a pet. The pet health record may be generated automatically from text in a veterinary practice management system.

One embodiment relates to training a pet medical text recognizer and using it to classify text according to a standardized coding scheme for pet health. The pet medical text recognizer may include one or more machine learning classifiers. The machine learning classifiers may be trained using training data from a veterinary practice management system. The performance of the machine learning classifiers may be evaluated according to a performance metric and the highest performing classifier selected as the model for the pet medical text recognizer. New text from the veterinary practice management system may be input to the pet medical text recognizer to generate codes for the text. The codes may be aggregated into a pet health record.

BRIEF DESCRIPTION OF THE DRAWINGS

FIG. 1 illustrates an exemplary veterinary practice management system.

DETAILED DESCRIPTION

Figure 2:
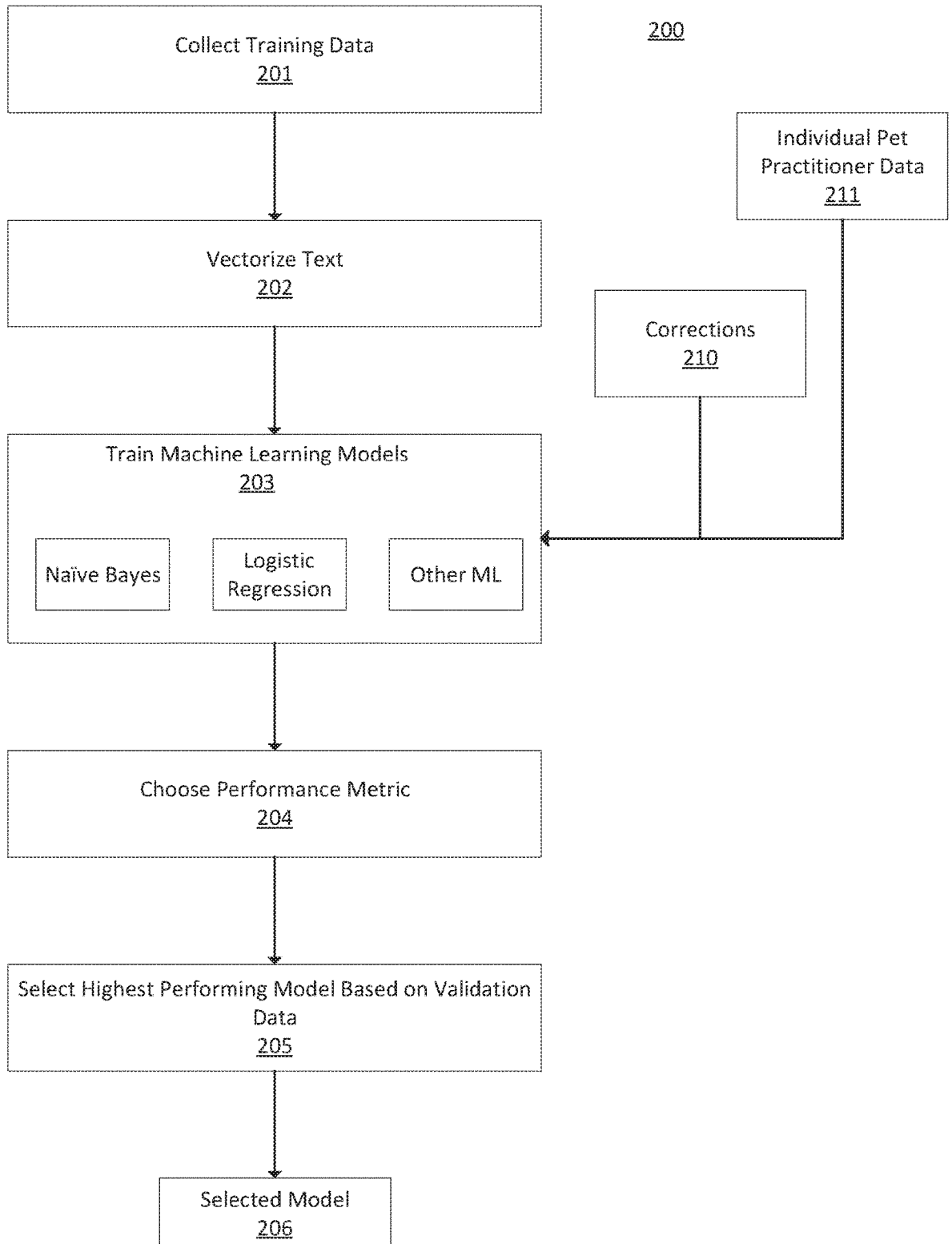
FIG. 2 illustrates an exemplary method for training a pet medical text recognizer and selecting a machine learning model.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

FIG. 1 illustrates an exemplary veterinary practice management system 100 that may be used in some embodiments. A veterinary practice management system 100 is a software system installed on computer hardware that helps veterinary practitioners manage their veterinary practices. The veterinary practice management system 100 may be installed on a local computer in the veterinary practice, on a remote server, or in the cloud.

The veterinary practice management system 100 may store a variety of information about the veterinary practice. The veterinary practice management system 100 may include patient storage 101 for storing information about patients, such as pets, client storage 102 for storing information about clients, such as pet owners, invoice storage 103 for storing invoices that are sent to clients, schedules and appointment storage 104 for storing information about the schedules and appointments of veterinary health practitioners in the veterinary practice, reminders storage 105 for storing reminders for the veterinary health practitioners in the veterinary practice, medical notes storage 106 for storing medical notes written by the veterinary health practitioners, and pet health records storage 107. The storage elements 101-107 may be database storage such as tables or may be non-table data structures, such as in a NoSQL database. The storage elements 101-107 may take the form of a variety of data structures and may store text, images, videos, and other multimedia.

The veterinary practice management system 100 may present information to the veterinary practitioners through user interfaces including graphical elements, forms, fields, and interactive components. Veterinary practitioners may use user interface elements to enter data for storage in storage elements 101-107 or to modify or delete data that is currently stored.

In an exemplary method of use, a new client joins the veterinary practice and goes through intake. A veterinary practitioner enters information about the client, including name, address, contact information, and other demographics into client storage 102. The veterinary practitioner also enters information about the patient, the client's pet, into patient storage 101. During the appointment, the veterinary practitioner may record medical notes about the patient, which are stored in medical notes storage 106. Medical notes may include text describing the diagnosis of the pet and also what treatments were applied or are recommended in the future. The medical notes include an identifier of the patient and client to link to the records in the patient storage 101 and client storage 102. The veterinary health practitioner may schedule future appointments, which are stored in schedule and appointment storage 104. Appointments may include a date, time, patient, client, and description of the purpose of the appointment and optionally the treatment to be applied. The veterinary practitioner may also enter reminders in reminder storage 105. Reminders may include a date, time, patient, client, and description of the purpose of the reminder and optionally the treatment to be applied. After the appointment, the veterinary health practitioner may prepare and send an invoice to the client, which is stored in invoice storage 103. The invoice may include text describing the type of treatments provided. Using methods herein applied to the data in the veterinary practice management system 100, a pet medical text recognizer may generate a pet health record and store it in the pet health records storage 107.

FIG. 2 illustrates an exemplary method 200 that may be performed in some embodiments. Initially, a classification system of pet clinical events may be provided, which may classify clinical events into standardized codes. Clinical events may include treatments, such as vaccinations, medications, and medical procedures, clinical findings, symptoms, diagnoses, and other events. Standardized codes may comprise, for example, SNOMED CT, ICD-9, ICD-10, and other existing coding systems or a custom coding system. In some embodiments, a classification system comprises a plurality of standardized codes that each uniquely correspond to a clinical event and each standardized code may comprise a unique alphanumeric code, a textual description, and/or an abbreviation.

In step 201, training data may be collected. Training data may comprise pairs of free form text and the associated standardized code or codes that correctly classify the text. For example, the text "Distemper/Parvo Titer K9-KSU" may be associated with the code "Distemper/Parvovirus (titer)", where the code represents the text in a standardized manner. The text may be written by a veterinary practitioner and the standardized code may be provided by a human or machine coder.

Some of the training data may be set aside as validation data. Validation data is used for validation of the performance of the machine learning classifiers but is not used for training. Validation may be performed by performing inference on the free form text of the validation data pairs to obtain predicted codes. The predicted codes may be compared to ground truth codes to determine performance metrics regarding the performance of the algorithm, such as accuracy measures.

In step 202, the text component of the pairs are vectorized. Vectorization translates a textual representation into a feature vector. A variety of vector formats may be used such as bag of words and term frequency-inverse document frequency (TF-IDF). In an embodiment, the feature vector may comprise an array of numbers.

A pet medical text recognizer including one or more machine learning classifiers may be provided. The pet medical text recognizer may take vector representations of text as input and output an appropriate code from the classification system to identify the corresponding clinical event, such as a treatment that was performed. In step 203, the one or more machine learning classifiers of the pet medical text recognizer may be trained to classify text according to the classification system by using the training data, which associates text to their correct classifications. A variety of machine learning classifiers may be used in the pet medical text recognizer, such as Naïve Bayes, Logistic Regression, Neural Networks, Support Vector Machines (SVMs), Long Short-term Memory (LSTM), Bidirectional Long Short-term Memory (BLSTM), and other classifiers. The machine learning classifiers may use regularization such as L1 or L2 regularization. In some embodiments, multiple instantiations of a single type of classifier may be used, but the different instantiations may have different parameters. For example, multiple neural networks with different numbers of layers may be used.

It would be desirable for the pet medical text recognizer to be able to select the best machine learning classifier from the set of machine learning classifiers. In step 204, a performance metric may be chosen. The performance metric may be hard coded or may be configured. The performance metric may provide a method of comparing the performance of the multiple machine learning classifiers. A performance metric may comprise accuracy, recall, precision, F1 score, area under the curve (AUC), and other metrics.

In step 205, the performance of the one or more machine learning classifiers is evaluated using validation data. The highest performing machine learning classifier on the performance metric may be selected to perform classification as the selected model 206 of the pet medical text recognizer. In this manner, the system may automatically select the best model for classifying pet medical text. The use of multiple machine learning models, such as in steps 203-205, is optional and in some embodiments a single machine learning model is selected and used. In an embodiment with a single machine learning model, the machine learning model may be trained in step 203 and steps 204-205 may be skipped because there is only a single model to choose from.

In some embodiments, the pet medical text recognizer may continue to be improved through processing of corrections from veterinary practitioners. A user interface may be provided to veterinary practitioners where they may identify a misclassification of text and delete the misclassification. User interface components may be provided to add new classifications to the text or modify existing classifications.

Thus, the pet medical text recognizer may receive corrections 210. Each correction 210 may identify one or more misclassifications by the pet medical text recognizer, and each correction may comprise text, which had initially been misclassified, and a new classification. The one or more machine learning models of the pet medical text recognizer may be trained using the corrections.

In some embodiments, the pet medical text recognizer may be custom trained to recognize text from a particular veterinary practitioner. Each veterinary practitioner has a different writing style and personalizing the recognition model to a particular practitioner's writing style can increase accuracy. Therefore, the one or more machine learning models of the pet medical text recognizer may be custom trained for a plurality of veterinary practitioners by training the one or more machine learning classifiers for each veterinary practitioner using text written by the veterinary practitioner 211. The text written by the veterinary practitioner may be human coded with the appropriate code from the standardized coding scheme so that the text may be used as training data. The data of a particular veterinary practitioner is used to train the pet medical text recognizer for that particular veterinary practitioner and not used to train the pet medical text recognizer for other veterinary practitioners.

Alternatively, the data of a particular veterinary practitioner may be given a higher weight than training examples from other veterinary practitioners when training the pet medical text recognizer for that particular veterinary practitioner. The data of that particular veterinary practitioner may still be used to train the general pet medical text recognizer model, but at a lower weight than when being used for custom training for the particular veterinary practitioner.

In some embodiments, the pet medical text recognizer may be iteratively trained and cause it update its selection of the highest performing machine learning classifier. Training of the machine learning classifiers on additional training examples may be performed. The performance of the machine learning classifiers may then be evaluated on the validation data using the performance metric. The selection of the highest performing machine learning classifier may be updated based on the performance metric.

Figure 3:
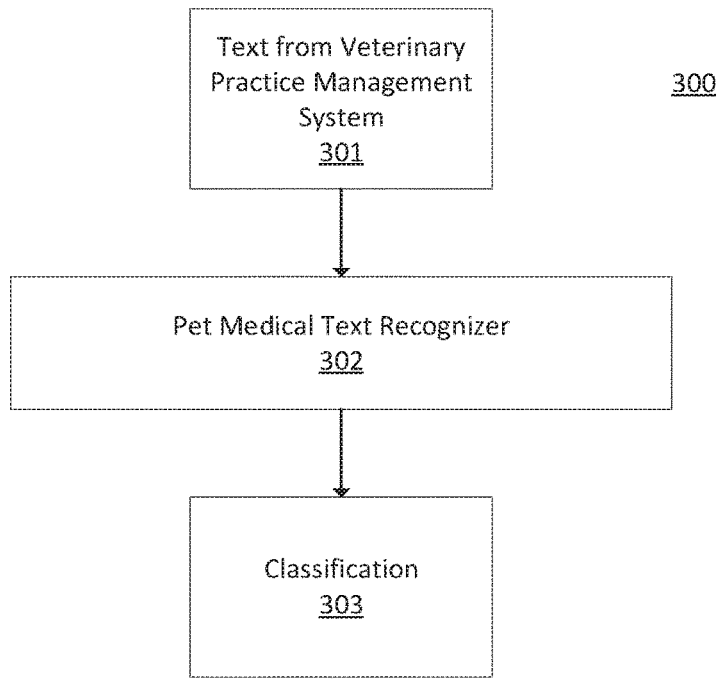
FIG. 3 illustrates an exemplary method for performing classification using a pet medical text recognizer.

FIG. 3 illustrates an exemplary method 300 for classifying text in a veterinary practice management system to identify a standardized pet clinical event code that should be applied to the text. Text from the veterinary practice management system 301 is received. Text may be, for example, text of a reminder, listings of line items on an invoice, an appointment, or a medical note. The text 301 is fed into the pet medical text recognizer 302 having one or more machine learning classifiers. The pet medical text recognizer 302 classifies the text from the veterinary practice management system 301 using the selected machine learning classifier 206 of the pet medical text recognizer to identify a pet clinical event classification 303.

Figure 4:
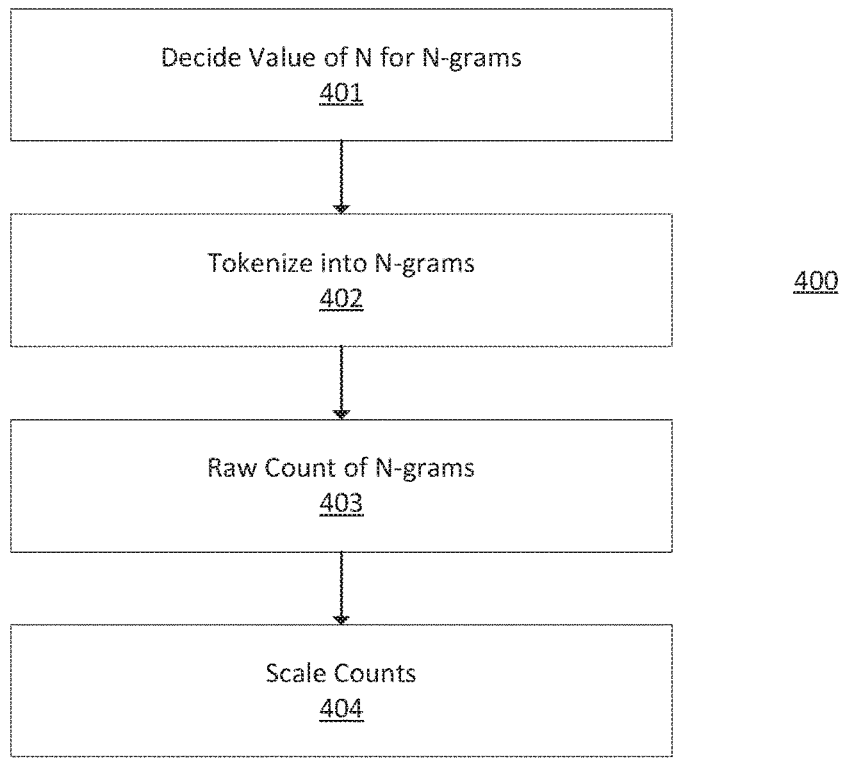
FIG. 4 illustrates an exemplary method for generating a feature vector from text.

FIG. 4 illustrates an exemplary method 400 for creating a vector from text. The vectors may be used during both training in method 200 and classification in method 300. In step 401, a value of n may be decided for producing n-grams. N-grams are groups of n adjacent characters or words that are treated as unit. Use of n-grams of characters may help address potential misspellings of words. Use of n-grams of words can provide additional features based on the context surrounding words. In step 402, text may be provided from the veterinary practice management system 301 and tokenized into n-grams of characters. In step 403, a bag of words vector may be created based on the raw counts of the n-grams of characters. In the bag of words model, each element of the vector may represent a raw count of the frequency of each n-gram, with each element corresponding to a specific n-gram. In step 404, the raw counts are scaled. Scaling may be performed using term frequency-inverse document frequency, which normalizes the raw counts and increases the weight of n-grams that appear infrequently.

While methods described above addressed classifying an entire block of text by transforming it into a vector, long blocks of text may include descriptions of many types of pet clinical events and therefore may be more successfully categorized in they could be divided into sub-blocks and classifications applied to the various sub-blocks.

Figure 5:
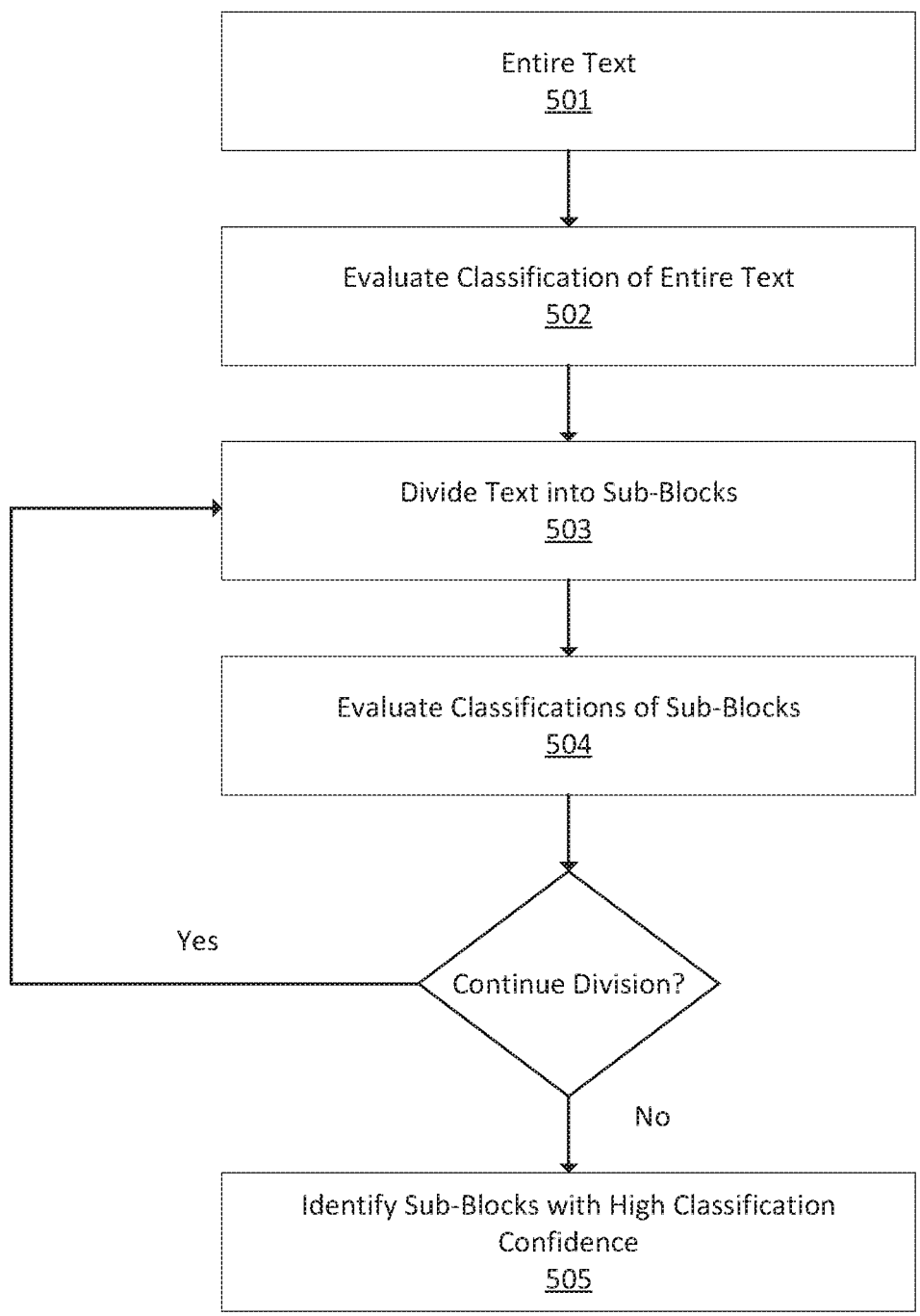
FIG. 5 illustrates an exemplary method for performing classification of sub-blocks of text from a longer piece of text.

FIG. 5 illustrates an exemplary method 500 for classifying a lengthy block of text by dividing it into sub-blocks and classifying the sub-blocks. In step 501, a portion of text 501 is provided. In step 502, classification is performed on the entire portion of text 501 using the pet medical text recognizer 302. In step 503, the portion of text 501 is divided into sub-blocks. In step 504, classification is performed on the sub-blocks using the pet medical text recognizer 302. The system then decides whether to continue dividing the text further into sub-blocks. If it decides to continue dividing, then the process continues at step 503 to continue dividing into smaller sub-blocks. If the system determines to stop dividing into sub-blocks, then in step 505 the system identifies the sub-blocks that were classified with highest confidence by the pet medical text recognizer 302. The system may then aggregate the classifications of the sub-blocks and assign the list of aggregated classifications to the overall portion of text 501.

The sub-blocks of portion of text 501 may also be viewed as sliding windows on the text. As discussed above, classification may be performed on a plurality of the sliding windows taken from the text.

The classification methods herein may be performed on text throughout a veterinary practice management system 100, such as text of invoices 103, schedules and appointments 104, reminders 105, and medical notes 106. The classifications may then be assigned to the patient (pet) and client (human owner) and dated according to data associated with the classified text. The classifications provide a standardized coding of pet health information. By listing these codes chronologically and associating them with a particular pet, a complete pet health record 107 may be generated automatically using machine learning.

The terminology used herein is for the purpose of describing particular aspects only and is not intended to be limiting of the disclosure. As used herein, the singular forms "a," "an," and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been particularly shown and described with reference to specific embodiments thereof, it should be understood that changes in the form and details of the disclosed embodiments may be made without departing from the scope of the invention. Although various advantages, aspects, and objects of the present invention have been discussed herein with reference to various embodiments, it will be understood that the scope of the invention should not be limited by reference to such advantages, aspects, and objects. Rather, the scope of the invention should be determined with reference to patent claims.

What is claimed:

1. A computer-implemented method for generating a pet health record, the method comprising:
providing a classification system of pet clinical events, the classification system configured to identify a pet clinical event classification;

providing a pet medical text recognizer configured to classify text, the pet medical text recocognizer that includes one or more machine learning classifiers, the one or more machine learning classifiers comprising at least a neural network, a Long Short-term Memory classifier, or a Bidirectional Short-term Memory classifier;

training one or more of the machine learning classifiers of the pet medical text recognizer to classify text according to the classification system using training data, the training data associating text and classifications;

providing a performance metric for comparing the one or more machine learning classifiers;

evaluating the performance of the one or more machine learning classifiers of the pet medical text recognizer using validation data and selecting a highest performing machine learning classifier according to the performance metric;

receiving the text input from a veterinary practice management system;

classifying the text from the veterinary practice management system using the one or more machine learning classifiers of the pet medical text recognizer to identify the pet clinical event classification.

2. The method of claim 1, wherein the one or more machine learning classifiers comprise at least one of naïve bayes, logistic regression, neural networks, or support vector machines (SVMs).

3. The method of claim 1, wherein the text from the veterinary practice management system comprises text from at least one of a reminder, an invoice, an appointment, or a medical note.

4. The method of claim 1, wherein the text from the veterinary practice management system is from a pet medical note and classification is performed on a plurality of sliding windows taken from the text.

5. The method of claim 1, wherein the text from the veterinary practice management system is converted to vector format.

6. The method of claim 1, further comprising:
tokenizing the text from the veterinary practice management system into n-grams of characters;
creating a bag-of-words vector based on the n-grams of characters;
scaling the bag-of-words vector based on term frequency-inverse document frequency (TF-IDF).

7. The method of claim 1, further comprising:
custom training the one or more machine learning classifiers of the pet medical text recognizer for a plurality of veterinary practitioners by training the one or more machine learning classifiers for each pet health practitioner using text written by the veterinary practitioner.

8. The method of claim 1, further comprising:
receiving corrections of one or more misclassifications by the pet medical text recognizer, the corrections comprising text and a new classification of a pet clinical event;
training the one or more machine learning classifiers of the pet medical text recognizer using the corrections.

9. The method of claim 1, wherein the classification system includes classifications for at least one of pet vaccinations, pet medications, or pet medical procedures.

10. The method of claim 1, further comprising:
iteratively training the one or more machine learning classifiers of the pet medical text recognizer;

evaluating the performance of the machine learning classifiers on the validation data according to the performance metric; and
updating the selection of the highest performing machine learning classifier according to the performance metric.

11. A non-transitory computer-readable medium comprising computer-executable instructions for generating a pet health record, the non-transitory computer-readable medium comprising computer-executable instructions for:
providing a classification system of pet clinical events, the classification system configured to identify a pet clinical event classification;
providing a pet medical text recognizer that includes one or more machine learning classifiers, the one or more machine learning classifiers comprising at least a neural network, a Long Short-term Memory classifier, or a Bidirectional Short-term Memory classifier;
training one or more of the machine learning classifiers of the pet medical text recognizer to classify text according to the classification system using training data, the training data associating text and classifications;
providing a performance metric for comparing the one or more machine learning classifiers;
evaluating the performance of the one or more machine learning classifiers of the pet medical text recognizer using validation data and selecting the highest performing machine learning classifier according to the performance metric;
receiving the text input from a veterinary practice management system;
classifying the text from the veterinary practice management system using the one or more machine learning classifier of the pet medical text recognizer to identify the pet clinical event classification.

12. The non-transitory computer-readable medium of claim 11, wherein the one or more machine learning classifiers comprise at least one of naïve bayes, logistic regression, neural networks, or support vector machines (SVMs).

13. The non-transitory computer-readable medium of claim 11, wherein the text from the veterinary practice management system comprises text from at least one of a reminder, an invoice, an appointment, or a medical note.

14. The non-transitory computer-readable medium of claim 11, wherein the text from the veterinary practice management system is from a pet medical note and the non-transitory computer-readable medium further comprises computer-executable instructions for performing classification on a plurality of sliding windows taken from the text.

15. The non-transitory computer-readable medium of claim 11, wherein the text from the veterinary practice management system is converted to vector format.

16. The non-transitory computer-readable medium of claim 11, further comprising instructions for:
tokenizing the text from the veterinary practice management system into n-grams of characters;
creating a bag-of-words vector based on the n-grams of characters;
scaling the bag-of-words vector based on term frequency-inverse document frequency (TF-IDF).

17. The non-transitory computer-readable medium of claim 11, further comprising instructions for:
custom training the one or more machine learning classifiers of the pet medical text recognizer for a plurality of veterinary practitioners by training the one or more machine learning classifiers for each pet health practitioner using text written by the veterinary practitioner.

18. The non-transitory computer-readable medium of claim 11, further comprising instructions for:
- receiving corrections of one or more misclassifications by the pet medical text recognizer, the corrections comprising text and a new classification of a pet clinical event;
- training the one or more machine learning classifiers of the pet medical text recognizer using the corrections.

19. The non-transitory computer-readable medium of claim 11, wherein the classification system includes classifications for at least one of pet vaccinations, pet medications, or pet medical procedures.

20. The non-transitory computer-readable medium of claim 11, further comprising instructions for:
- iteratively training the one or more machine learning classifiers of the pet medical text recognizer;
- evaluating the performance of the machine learning classifiers on the validation data according to the performance metric; and
- updating the selection of the highest performing machine learning classifier according to the performance metric.

\* \* \* \* \*